United States Patent [19]
Weisker

[11] Patent Number: 5,436,386
[45] Date of Patent: Jul. 25, 1995

[54] HYBRID SAFFLOWER PRODUCTION UTILIZING GENETIC DWARF MALE STERILITY

[75] Inventor: Arthur C. Weisker, Woodland, Calif.

[73] Assignee: Seedtec International Inc., Woodland, Calif.

[21] Appl. No.: 131,619

[22] Filed: Oct. 5, 1993

[51] Int. Cl.$^6$ .......................... A01H 5/00; A01H 1/00; A01B 79/00; A01C 1/00
[52] U.S. Cl. ................................... 800/200; 800/255; 47/58
[58] Field of Search ............... 800/200, 205, 250, 255, 800/DIG. 9, 69; 47/58.01, 58.03, DIG. 1

[56] References Cited

U.S. PATENT DOCUMENTS 4,751,347  6/1988  Erickson ........................... 800/200

OTHER PUBLICATIONS

Nerkar et al. 1985, J. Maharashtra agric. Univ. 10(1): 71–74.
Ebert et al. 1966, Crop Science, 6: 579–582.
Ramachandram et al. 1991, Indian J. Genet. 51(2): 268–269.
Heaton et al. 1982, Crop Science, 22: 550–522.
Carapetian et al, 1976, Crop Science, 16: 395–399.
Deokar et al, 1975, Botanique, VI(2+3): 165–168.
Heaton et al, 1980, Crop Science, pp. 20: 554.
Stuber, 1980, In: Hybridization of Crop Plants. Fehr et al., eds. pp. 84–85.
Claassen, C. E., "Natural and Controlled Crossing in Safflower," Agronomy Journal, 42(8): 381–384 (1950).
Rao, V. R., "Combining Ability for Yield, Percent Oil and Related Components in Safflower," Indian Journal of Genetics, 43: 68–75.
Rubis, D. D., "Development of Hybrid Safflower," Proceedings, Third Safflower Research Conference, University of California, Davis, pp. 27–32, (1969).
Urie, A. L. et al., "The Performance of Hybrid Safflower in Competitive Yield Trials," Proceedings, Third Safflower Research Conference, University of California, Davis, pp. 54–56, (1969).
Hill, A. B., "Hybrid Safflower Breeding," Proceedings of the Third International Safflower Conference, Hyderabad, India, pp. 169–170 (1989).
Deshmukh, R. M. et al., "Commercial Scale Exploitation of Hybrid Vigour in Safflower using Genetic Male Sterility System," Proceedings Of The Second International Safflower Conference, Hyderabad, India, pp. 163–167 (1989).
Rubis, D. D., "Effects of Honey Bee Activity and Cages on Attributes of Thin–Hull and Normal Safflower Lines," Crop Science, 6:11–14 (1966).

*Primary Examiner*—David T. Fox
*Assistant Examiner*—Erich E. Veitenheimer
*Attorney, Agent, or Firm*—Hollie L. Baker

[57] ABSTRACT

The invention is directed to the identification of a safflower gene that exhibits male sterility in combination with a morphologically identifiable dwarfism in the male sterile plant and to the production of hybrid safflower that uses this safflower gene.

14 Claims, 3 Drawing Sheets

HYBRID SAFFLOWER PRODUCTION UTILIZING GENETIC DWARF MALE STERILITY

FIELD OF THE INVENTION

This invention is in the field of agronomy, specifically safflower plant breeding. The invention is directed to the identification of a safflower gene that exhibits male sterility in combination with a morphologically identifiable dwarfism in the male sterile plant and to the production of hybrid safflower that uses this safflower gene.

BACKGROUND OF THE INVENTION

The safflower plant (Carthamus tinctorius L) is predominantly self pollinated. With self pollination, the pollen from the anthers is transferred to the stigma of the same flower, or to a flower on the same plant. To produce a hybrid from true breeding inbred male and female parents of self pollinating plants requires that the female parent be male sterile. In research test settings this can be accomplished by individual plant manipulations. Hybrids produced from different varieties of the same species (F1 hybrids) are often more vigorous than either parent, so although they cannot breed true, they are favored by the agriculturalist.

The potential of hybrid safflower has been known for many years. In 1950, Claassen (C.E. Claassen, "Natural and Controlled Crossing in Safflower, Carthamus tinctorius l.," *Agronomy Journal*, 42(8):381-384 (1950)) suggested using low fertility lines as female parents in a hybrid production scheme. In the intervening years many publications have used genetic analysis to indicate inheritance patterns for yield as well as yield components. Though there are differences in opinion regarding components of variation, it was commonly concluded that hybrid systems would appreciably improve the performance of safflower as reported, for example, in V.R. Rao, "Combining Ability for Yield, Percent Oil and Related Components in Safflower," *Indian Journal of Genetics*, 43:68-75 (1983).

Several researchers have proposed breeding systems which would enable safflower to be utilized as a hybrid crop. The first system was researched by Rubis in the 1960's. This system exploited the low fertility gene "th" as a female in a hybrid system. A summary of this program is detailed in D.D. Rubis, "Development of Hybrid Safflower," *Proceedings, Third Safflower Research Conference*, University of California, Davis, pages 27-32 1969). The advantages of the hybrid, as well as self-fertility problems with the female, were discussed by Urie and Zimmer (A.L. Urie and D.E. Zimmer, "The Performance of Hybrid Safflower in Competitive Yield Trials," *Proceedings, Third Safflower Research Conference*, University of California, Davis, pages 54-56 (1969)). This self pollination problem, along with low yields in hybrid production fields, eventually caused the program to be ended unsuccessfully.

Other hybrid programs have been pursued in recent years. A program undertaken by Cargill Seeds and Agrigenetics over the past 20 years utilizing a cytoplasmic male sterility (cms) system has produced high yielding hybrids, but no commercially available hybrids to date. With cytoplasmic inheritance, a characteristic is determined by genes in the cytoplasm (plasmagens) rather than in the nucleus. These characteristics are normally transmitted through the female gamete, which contributes most of the cytoplasm to the zygote. The male gamete only contributes to the nucleus. A summary article describing the program is reported in A.B. Hill, "Hybrid Safflower Breeding," *Proceedings of the Second International Safflower Conference*, Hyderabad, India, pages 169-170 (1989).

In India, safflower hybrids are available using as a female parent the genetic male sterile system (gms) based on UC148, a gms line released from University of California at Davis. (R.M. Deshmukh and N. Nimbkar, "Commercial Scale Exploitation of Hybrid Vigour in Safflower using Genetic Male Sterility System," *Proceedings of the Second International Safflower Conference*, Hyderabad, India, pages 163-167 (1989)). This system requires visual identification and hand roguing of male plants at anthesis, the period from flower opening to fruit set, in order to establish a pure stand of female plants. This method requires excess labor expense to ever be feasible in the USA.

Safflower is an important oilseed crop. A continuing goal of safflower breeders is to improve the crop through hybrid breeding techniques by identifying an effective male sterile plant for use in producing hybrids.

SUMMARY OF TEE INVENTION

Through an intensive breeding program, a gene in safflower was identified that exhibits male sterility in combination with morphologically identifiable dwarfism. The unique feature of the gene is its sterility coupled pleiotropically with morphological characteristics which allows early and effective removal of fertile plants in a hybrid production field, making possible an efficient and cost effective means of hybrid production. The sterility of the gene is unrelated to any other source of male sterility known in safflower.

The invention is thus directed to this gene and a process of utilizing the gene in safflower plants to breed and produce hybrid safflower seed. The invention also includes the process by which commercial production of hybrid safflower can be accomplished in varieties using the gene as the female parent. The invention is further directed to plants, seed, and oil from the dwarf male sterile seed and hybrid seed which contain or are derived from plants or seed which contain the gene.

DEFINITIONS

In this specification, a number of botanical terms are used. In order to provide a clear and consistent understanding of the specification and claims, including the scope to be given such terms, the following definitions are provided:

Chi-squared test ($X^2$ test) or chi-squared. A test used to find how well observed frequencies of results correspond with expected frequencies. It is used when the observations fall into discrete classes, such as dwarf or normal height. Chi-squared is found by calculating (observed-expected)$^2$/expected for each class and adding these together. The sum is then checked in the table of $X^2$ values for different degrees of freedom at various probability levels.

Roguing. To remove and destroy any plant that varies from the rest of the crop and is consequently not wanted.

Pleiotropism. The control of several apparently unrelated characteristics by a single gene. In the description of the invention, pleiotropy is considered the mode of gene action, although the possibility of an extremely tight linkage cannot be completely eliminated.

Segregation ratios. The proportion of one type of offspring to another that occurs as a result of separation of alleles at meiosis.

Genotype. The genetic composition of a plant.

Phenotype. The expressed characteristics of a plant, typically its physical appearance.

Male sterility. A condition in which pollen production is prevented by mutation of one or more genes governing its formation. Male sterility is employed by plant breeders as a method of ensuring cross pollination and hence F1 hybrid production.

Anthesis. The period from flower opening to fruit set.

DETAILED DESCRIPTION OF THE INVENTION

I. INTRODUCTION: FIELD TESTS

Figure 1:
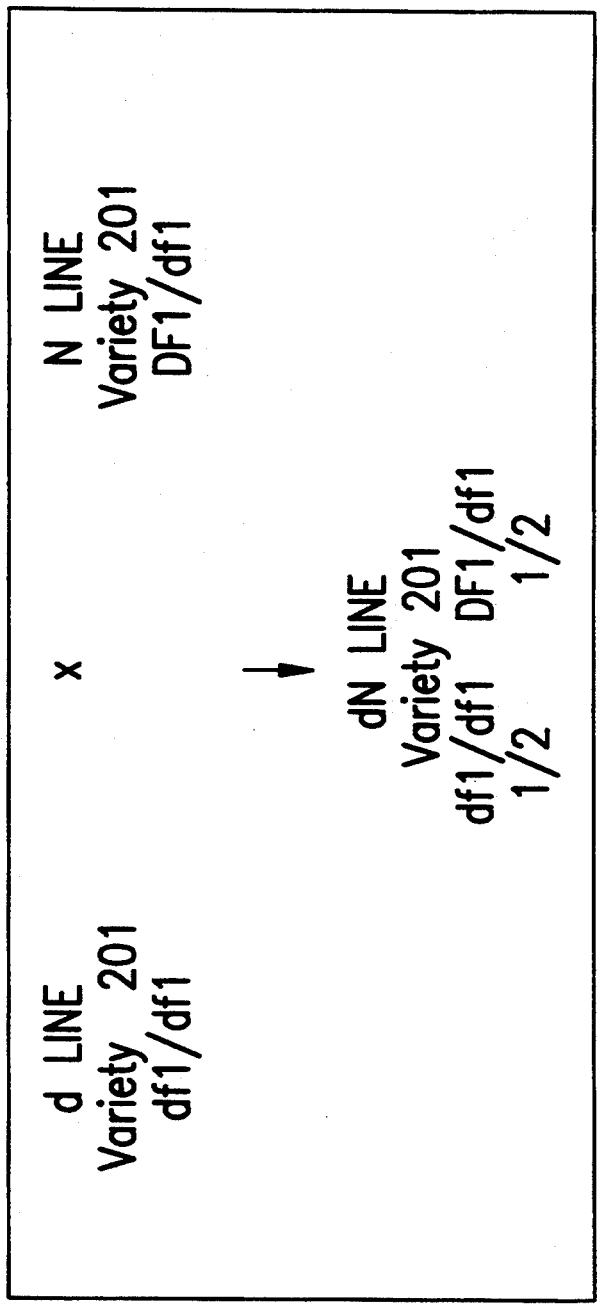
FIG. 1 is a diagram of the maintenance of dN lines of the dNS system.

A long term project in the applicant's safflower breeding program was to find a suitable female parent in a hybrid breeding program. One dwarf type was noticed to set poor selfed seed over a number of years. Ten rows were planted to determine if the plants were in fact male sterile. In the ten rows 6 had dwarf plants that appeared to be male sterile while dwarf plants in the other 4 were male fertile. Sibling (sib) crosses were made in two of the dwarf sterile rows. Other rows which had sterile dwarf plants were not continued due to seed set in the dwarf line or a lack of seed set in sib crosses. In the breeding nursery, dwarf plants were observed to be male sterile, while normal sized siblings were male fertile. Sibling (sib) crosses were made with the dwarf male sterile plants and the normal sized male fertile siblings, and the plants resulting from the sib crosses set seed. In the breeding nursery, the seed from the sib crosses and selfed seed of the male parent were planted (year 1).

Analysis of the plants using segregation ratios showed that the results were consistent with those of a single recessive gene controlling the dwarf phenotype (see Table 1). Six crosses were made. In three crosses, the cross segregated for dwarf and normal plants. Plants from the male parent of these crosses also segregated. In two cases, the cross failed to segregate as did plants from the male parent. The number of plants at this point was too low to provide statistical evidence for the mode of gene action. Data provided below confirms the single recessive nature of the gene. In the breeding nursery in year 2, further crosses were made within lines as well as initial backcrosses onto cultivated lines.

TABLE 1

| 89 ROW | DWARF/NORMAL RATIOS FROM CROSSES MADE IN YEAR 1 | | |
|---|---|---|---|
| | PARENTAL LINES | NO. DWF PLANTS | NO. NORMAL PLANTS |
| 455 | 12-4 × 12-2 | 4 | 6 |

TABLE 1-continued

| 89 ROW | DWARF/NORMAL RATIOS FROM CROSSES MADE IN YEAR 1 | | |
|---|---|---|---|
| | PARENTAL LINES | NO. DWF PLANTS | NO. NORMAL PLANTS |
| 456 | 12-2 | 3 | 16 |
| 459 | 12-2 × 12-7 | 8 | 14 |
| | 12-7 | 2 | 13 |
| 461 | 12-4 × 12-8 | 0 | 16 |
| 462 | 12-8 | 0 | 23 |
| 463 | 12-3 × 12-8 | 0 | 21 |
| 464 | 12-8 | 0 | 16 |
| 465 | 12-2 × 13-4 | 4 | 3 |
| 466 | 13-4 | N/A | N/A |
| 467 | 12-2 × 13-5 | 0 | 7 |
| 468 | 13-5 | 0 | 22 |
| 469 | 12-2 × 13-6 | 12 | 25 |
| 470 | 13-6 | 5 | 15 |

Segregation ratios in the year 3 breeding nursery supported the hypothesis of a single recessive gene controlling the dwarf sterile trait. A 1:1 ratio of dwarf plants to normal height plants is expected for a dwarf x normal cross, and a 3:1 ratio is expected for a selfed heterozygous normal height plant. The observed ratios (see Table 2) were very close to expected ratios. Combined data for crosses and for selfed normal plants fell very close to the expected ratios for a single recessive gene.

TABLE 2

| SEGREGATION FOR DWARF AND NORMAL SIZED PLANTS IN YEAR 3 | | |
|---|---|---|
| SEGREGATING LINE | NO. DWF | NO. NOR. |
| BULK DWARF × NORMAL PLANTS | 63 | 64 |
| SELFED NORMAL PLANTS FROM YEAR 2: | | |
| 455-1 | 21 | 45 |
| 455-3 | 11 | 16 |
| 455-4 | 6 | 20 |
| 459-1 | 9 | 31 |
| 459-2 | 2 | 20 |
| 459-3 | 8 | 24 |
| 461-1 | 9 | 41 |
| 461-2 | 11 | 19 |
| 463-1 | 13 | 32 |
| 469-1 | 5 | 15 |
| 470-1 | 2 | 17 |
| 471-1 | 9 | 23 |
| 471-4 | 4 | 8 |
| TOTAL | 110 | 311 |

CHI SQUARE = 0.278

In year 4, small scale increases were made for two hybrids and three female lines. Dwarf lines were planted in isolation in a commercial field to produce hybrid seed. Two dwarf sterile increases were planted in isolation, and a third dwarf sterile was planted under a cage in the breeding nursery. The cage measured 100 feet by 20 feet and was covered with mesh screen in order to exclude honeybees and other unwanted pollinating vectors. Bees were added to the cage at bloom for pollination. Later in year 4, seed from these increases was grown out to determine the potential of the dwarf plants as female parents for a hybrid, as well as to further determine the genetics of the dwarf gene (Table 3).

TABLE 3

| YEAR 4 GROWOUT READINGS FOR THREE DWARF LINES | | | | |
|---|---|---|---|---|
| LINE | NO. DWF | NO. NOR. | EXPECTED RATIO | CHI SQUARE |
| DWF2-6-4 | 19 | 55 | 3:1 | 0.0 |

TABLE 3-continued

| LINE | NO. DWF | NO. NOR. | EXPECTED RATIO | CHI SQUARE |
|---|---|---|---|---|
| YEAR 4 GROWOUT READINGS FOR THREE DWARF LINES | | | | |
| DWF2-6-4 NORMAL BULK | 329 | 522 | 2:1 | 9.73 |
| DWF2-6-4 DWARF PLANTS | | | | |
| DWF2-6-4 × S-555 | 10 | 632 | 98.6% HYBRID | 0.31 |
| DWF3-1-1 NORMAL BULK | 19 | 61 | 3:1 | 0.06 |
| DWF3-1-1 DWARF PLANTS | 272 | 256 | 1:1 | 0.48 |
| DWF3-1-B NORMAL PLANTS | 11 | 69 | 3:1 | 5.4 |
| DWF3-1-B DWARF PLANTS | 1145 | 1156 | 1:1 | .05 |
| DWF3-1-B × S-518 | 2 | 198 | 99% HYBRID | 0.02 |

The results indicate single recessive gene control of the trait. All of the segregating lines except two had a chi-squared value of less than 1. The year 4 increase of DWF2-6-4 had a single heterozygous fertile plant as the sole source. With the greater number of hybrids produced in year 4, this line segregated in nearly a perfect 3:1 ratio: 144 fertile normal height plants to 43 dwarf sterile plants. The other significant chi-squared value probably arose from the small size of the sample population. Importantly the hybrids had a very high degree of purity: hybrid percentages above 98% are considered excellent.

Additionally, the breeding nursery work focused heavily on the sterility of the dwarf safflower lines. In all hand crosses, self fertility of the dwarf plants was monitored by covering some heads with a plastic bag which excluded sources of cross pollination. The dwarf plants were consistently self sterile. More quantitative analysis regarding the gene for sterility is provided in Example 1 below. In addition, the stigmas of the dwarf plants were healthy looking and plentiful.

After the year 4 growouts were analyzed, the inventors began to seriously consider this program as a viable way to produce hybrid safflower. This hybrid technique would need to include a practical way of producing hybrids; nomenclature to identify lines; procedures to work with the gene; and quantification and additional identification of the properties of the dwarf gene.

II. DESCRIPTION OF THE DWARF GENE

The dwarf safflower gene with male sterility of this invention is called "df1". The dwarf sterile trait is expressed in the recessive genotype (df1/df1) and is completely recessive or almost completely recessive to the normal phenotype (DF1/DF1 or DF1/df1).

A second dwarf gene, which appears to be allelic with df1, was given the name df2. Plants with the genotype df2/df2 are also dwarf plants, but are male fertile. Plants with the genotype df2/df2 crossed onto sterile plants with the genotype df1/df1 result in an F1 plant which is a male fertile dwarf. F2 plants from this cross are dwarf plants segregating for male sterility.

A plant with the df1/df1 genotype is dramatically different phenotypically from an isogenic plant with the genotype DF1/—. Of 13 characteristics studied (see Table 4 below) in isogenic lines 11 were significantly different between df1/df1 plants and DF1/— plants. Most differences can be subcategorized into 2 divisions: (1) effects due to dwarfism and (2) effects due to sterility. Either a very tight linkage or pleiotropic effects account for the main differences. Observation of thousands of plants has not uncovered any evidence of a tight linkage.

Dwarf plants of this invention are 50–60% of the height of normal sized plants for particular safflower variety. Safflower varieties are not all the same height, so that a dwarf sized plant of one variety may, in fact, be the same height as another normal size safflower variety. The reduced height derives from shorter internodes and fewer branches in the df1/df1 plant. Dwarf plants have an internode length that is 50–60% of normal height plants and they have 10–20% fewer branches. The dwarfness characteristic also affects the total plant weight which in the dwarf is 25% or more lower than in normal height plants; head number per plant which is 10–20% lower; and head diameter which is 10% less.

The second important pleiotropic effect of the df1 gene is male sterility of df1/df1 plants. When covered by DELNET bags to insure self pollination, df1/df1 plants yield about 1 seed for each 10 heads bagged, which is less than 2% self fertility, compared to over 65 seeds in DF1/df1 plants. The mechanism of this sterility is not certain, but pollen is not visible on df1/df1 plants. When a dwarf plant is dissected open and the anther walls ruptured pollen is visible. It is not known whether the pollen is viable. The field tests, described above, have shown that pollen is not normally available for pollination. Days to anthesis is another pleiotropic effect of the df1 gene. Homozygous recessive (df1/df1) plants bloom 5 to 7 days later than normal height (DF1/—) plants.

Sterility affects other morphological traits in sterile plants such as df1/df1 plants. See, for example, D.D. Rubis, "Effects of Honey Bee Activity and Cages on Attributes of Thin-Hull and Normal Safflower Lines," *Crop Science*, 6:11–14 (1966). Unless the crossing percentage of a sterile plant approaches 100% it will set significantly fewer seed than self pollinated plants. Safflower seed in the situation of low seed set grows larger than it normally would. This in turn affects a number of plant characteristics. Harvested seed from male sterile plants is longer and thicker than seed from fertile plants. Oil content of the sterile plant will be lower than the fertile since virtually no oil is found in the hull. The magnitude of these differences will vary by variety, but will be significantly different from self fertile plants unless crossing percentage is virtually 100%. The sterility of df1 is not related to any other known genetic male sterile in safflower. The only available sterile source for testing is UC148. Crosses between df1/df1 plants and UC148 plants segregate as expected for genes at two independent loci. F2 plants of this cross result in sterile plants that are normal height, something never seen in crosses involving only df1 plants.

III. BREEDING SYSTEM USING THE df1 GENE

To describe a breeding system of this invention using the df1 gene the different types of breeding lines must be defined. The name of the breeding system is called the "dNS" system. The three component types of plants are the "d" plants, the "N" plants, and the "S" plants.

d plants are the dwarf sterile plants: any safflower plant with the genotype df1/df1. In the hybrid system these will be the female plants used to make the hybrid. A line that is a d line has the letter "d" coming before the variety name. For example, d plants of breeding line 101 are denoted d101.

N plants are plants heterozygous for the df1 gene: any plant with the genotype DF1/df1. In the breeding system, N plants pollinate d plants to renew the female source. A cross of d×N will result in a 1:1 mix of d plants and N plants. This seed (dN) will be planted as the female in hybrid production. A plant which is an N plant has the letter "N" preceding the variety number. For example, N plants of breeding line 101 are denoted N101. N plants can also be used as the female in hybrid production since selfed N plants segregate in a ratio of 3 N plants to 1 d plant. It should be noted that commercial hybrid seed will have the genotype of an N plant. N plants are integral to the creation and maintenance of d lines, but are not necessary for hybrid production.

The seed used to plant a hybrid field is an equal mixture of d plants and N plants. For this reason the planting seed will have both letters preceding the variety number as shown in FIG. 1. Line 201 planted in a seed production field will be denoted dN201. As the plants grow the phenotypes (and genotypes) of d and N plants become distinct. In a hybrid seed production field, the N plants will be rogued leaving only d plants. At this point the line will be called d201.

Figure 2:
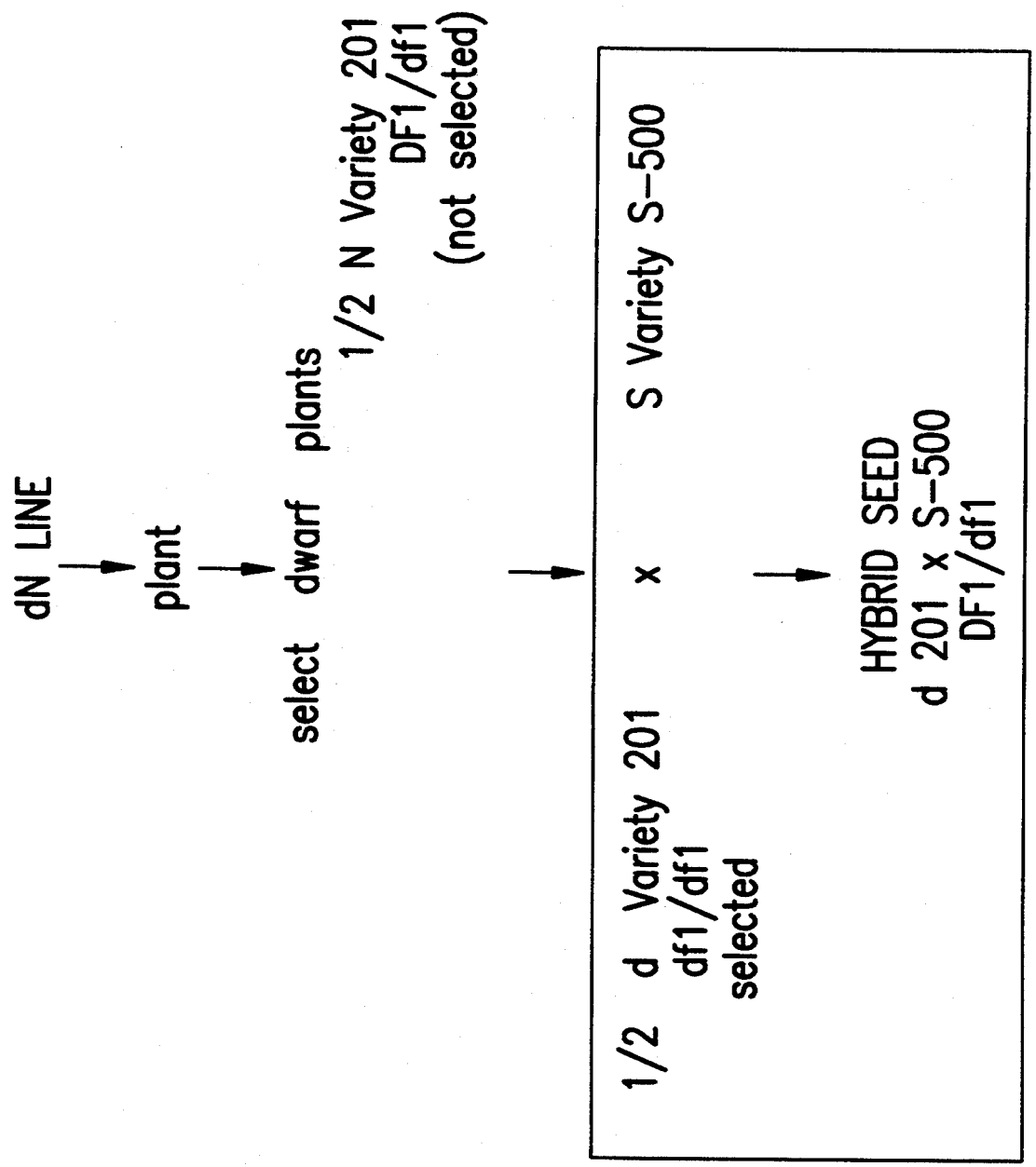
FIG. 2 is a diagram of safflower hybrid production using the dN line and the S line of the dNS system.

S plants: Any plant homozygous DF1/DF1 is an S plant. This includes all commercial varieties and germ plasm sources. S plants are the pollinators in hybrid production. The letter "S" again precedes the variety number. For example, line 500 used as a hybrid pollinator is denoted S-500. The pedigree of the hybrid made between S-500 and female d201 is d201 x S-500 as shown in FIG. 2.

The dNS system has a functional equivalent in the ABR system used in sunflower and sorghum hybrid breeding. In both systems, the female plant is given a name (d and A respectively); the line used to maintain the female parent has a name (N and B respectively); and the line used to pollinate the female and provide hybrid seed has a name (S and R respectively). This similarity is helpful in picturing the function of each seed type in the new system. The two systems, of course, work in different ways. Among the differences between the two systems are the cytoplasmic differences which distinguish A and B lines while genetic differences distinguish d and N lines. The dNS system has two types of planting seed, S seed and dN seed, while the ABR system has three, A seed, B seed, and R seed. The dNS system cannot currently provide planting seed which is 100% male sterile, while the ABR system can.

In addition to its use in a hybrid program the df1 gene can be used for other breeding purposes such as creating populations or any other program which utilizes male sterility.

Creating d and N lines can be done in three different ways. New lines can be created by (1) backcrossing, (2) by crossing with an S line or (3) by intercrossing two or more dN lines.

Backcrossing is an important and basic means of creating new dN lines. A modified an 9130 backcross procedure is used to create new dN lines. A d line is the nonrecurrent parent. Aris line is the recurrent parent. After intercrossing the two lines, the F1 progeny is selfed. Sterile plants in the segregating F2 are crossed using S line pollen to make the first backcross (BC1). The BC1 F1 is again fertile; it is selfed; and the F2 again segregates. This procedure is repeated five times or more until the N plants can be considered isogenic to the S line, or practically so. Crosses are made within rows, then progeny tested. Selections that are segregating 1:1 and visually acceptable are bulked to form the new variety. Backcrossing using df1 differs from standard backcrossing at this point since heterozygous plants are selected while homozygous plants are discarded. In standard backcrossing, homozygous plants are selected while heterozygous plants are discarded.

Additionally the dN line can be used to combine the genetic dwarf male sterility with one or more desirable plant phenotypes or genotypes for use in the hybrid safflower system. For illustration, characteristics such as erect branching, oil content, head number, etc., from one or more safflower varieties having these traits can be genetically bred into a line carrying the dwarf male sterile gene. Further, the genetic dwarf male sterile characteristic can be combined with a genetic male sterile safflower characteristic.

Analogous breeding techniques are used to create dN lines derived from d x S crosses or d X N crosses. F1 plants from a d x S cross are N lines. Fertile F1 plants of a cross between a d line of variety and an N line of a second variety are also N lines. Selection begins with the F1 N lines so the breeding plan is the same for either type of initial cross. Any breeding technique applicable for self pollinating varieties can be used, as well as breeding schemes designed for hybrid systems.

An important part of the selection process in the breeding system designed to create new dN lines is to screen dwarf sterile plants frequently to assure that the sterility is maintained. It is unknown if modifier genes with small effects exist that influence the df1 gene. The fact that 2% selfing occurs implies that fertility restoration genes may be present. It is therefore prudent to screen for sterility throughout the breeding process. This screening can be done by covering several heads of each selected dwarf plant with a DELNET bag to assure that no cross pollination occurs. At harvest, the bagged heads are threshed separately. Plants that set significant numbers of selfed seed are eliminated from the program.

Figure 3:
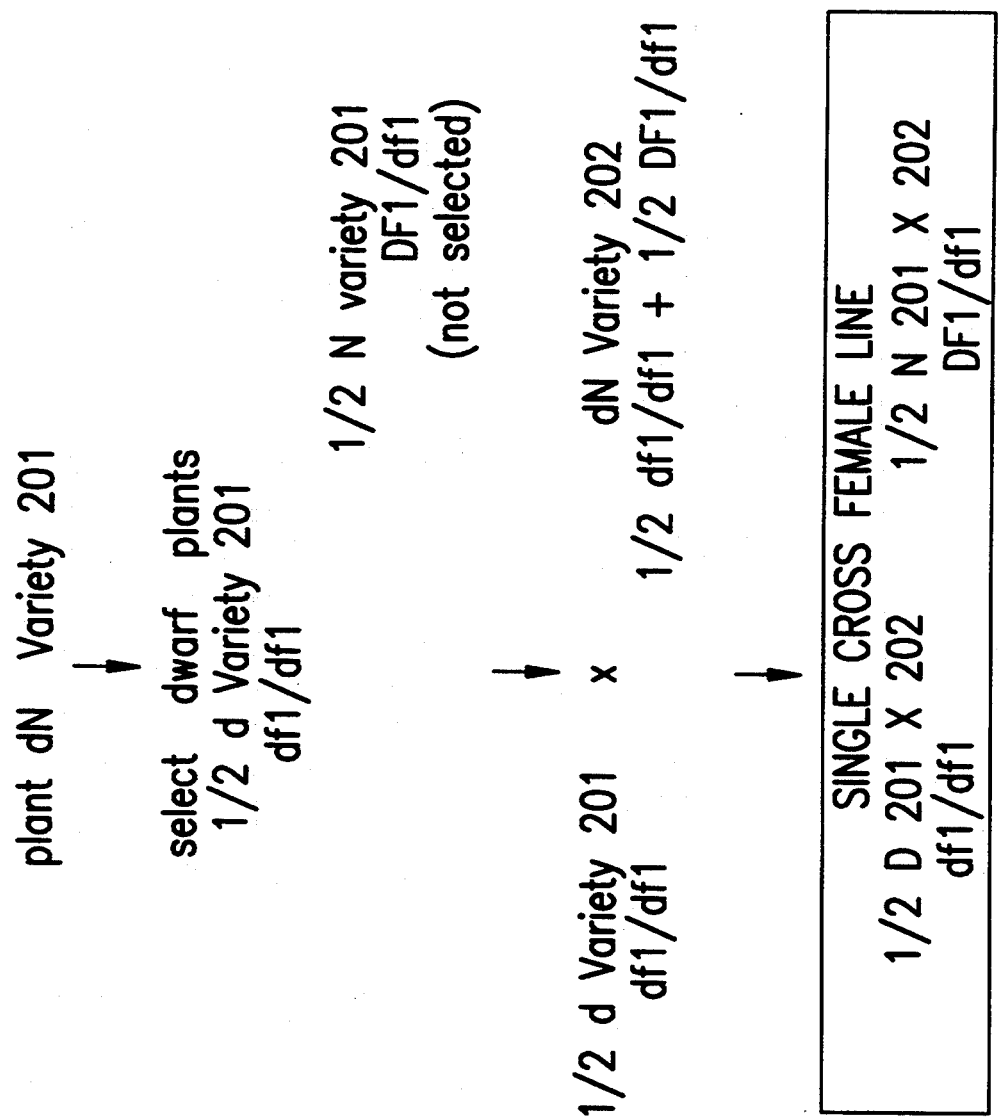
FIG. 3 is a diagram of the single cross female production of safflower plants of the dNS system.

It is critical in a production system to attain adequate yields in a hybrid production program. The earlier discussion regarding the characteristics of the dwarf sterile plants mentioned lower seed set in the dwarf plants. Selection for high crossing percentage is one way to increase yield. Single cross lines are another way to increase yield as shown in FIG. 3. In many crops single cross lines, due to hybrid vigor, are known to increase yields of female lines. Single cross lines can be utilized in the df1 breeding system. When a d line of one variety is pollinated by an N line of a second variety, the resulting dN line is a single cross line of the two varieties. For example, a cross of d plants of variety 201 crossed by N plants of variety 202 would give the single cross line dN(201 x 202).

Breeding S lines involves techniques currently available for use in safflower. Techniques used in hybrid programs such as recurrent selection are important in developing new pollinators for the dwarf lines.

IV. HYBRID PRODUCTION TECHNIQUES USING df1 GENE

Production techniques for hybrid safflower using the df1 gene are similar to those of other hybrid crops such as sunflower and sorghum. Planting dates are planned to insure the presence of pollen when the female blooms, isolation distances must be maintained, pollinating insects must be provided. Female lines and pollinators are interplanted in ratios that maximize seed yield. The pollinator must be harvested separately from the female after pollination to avoid seed contamination. To best produce hybrid safflower each of these steps must be adjusted to adapt to the unique nature of safflower and the df1 gene. The major differences are discussed below.

As mentioned above d plants bloom 5-7 days later than N plants. This difference can be significant in a production field. The bloom time of both parents must be known, and planting dates may need to be staggered in order to insure that pollen is available at the time that the d plants bloom and that it remains available throughout the bloom period.

Plant spacing in safflower usually is narrower than in other hybrid crops. A spacing between rows of 12"-30" and between plants within rows of 3"-6" will be most commonly used, although the spacing will vary according to the vigor of the female plants. For example, single cross lines can accept a wider spacing, while less vigorous lines require closer spacing. Accurate roguing of N plants from hybrid fields is critical. For speed and accuracy during roguing maintaining a precise distance between plants is important.

Rows of dN seed are interplanted with rows of S seed in the production field. A female to male planting ratio of 2:1, 3:1, or 4:1 is often used in hybrid production fields. The best choice is that which maximizes yield/acre of hybrid seed. It will often be necessary to leave one row on either side of the S line unplanted in order to prevent the S line from overgrowing the smaller d line and causing harvest difficulties or possible seed mixing at harvest.

As in other bee pollinated crops, it is necessary to place bee hives in the hybrid production field to insure cross pollination. One or two hives per acre is usually acceptable. It is also necessary to maintain an isolation distance between the hybrid field and any other safflower in order to prevent accidental outcrossing with unwanted pollen. A distance of one mile is considered minimal and an isolation of two miles or more is preferred.

After pollination is completed the S line and the d line should be harvested separately in order to prevent accidental seed mixing. This can be done by chopping the S plants while green or by harvesting them at a different time from the d lines.

The dN line planted in a production field will segregate in a 1:1 ratio for dwarf sterile d plants and normal fertile N plants. The primary challenge in hybrid production using df1 is to remove the N plants, leaving only d plants to be pollinated by S plants. This is the barrier that cannot be overcome economically in the case of normal gms lines in which male and female are indistinguishable except for the presence of pollen in the fertile and its absence in the sterile plants. The great advantage in the df1 system is that fertile and Sterile plants become distinct early in development. A trained observer can begin to see differences as early as the two leaf stage; more importantly an untrained person can easily be taught to differentiate N lines from d lines as early as 6 weeks after planting, before the plants are fully grown and well before anthesis. Height difference is the key to most methods of roguing, whether using manual labor or using mechanical methods that are described below.

1. Hand roguing: A hoeing crew can be quickly trained to cut the N plants and leave only d plants to be pollinated.

2. A device mounted on a tractor which uses an herbicide wick system. The tractor drives through the field with the wick mounted in such a way that the N plants are touched by the herbicide saturated wick, while the d plants are avoided. The N plants die, leaving only d plants to be pollinated.

3. A device exists which uses a metal rod charged with electricity to kill the N plants. The system is again mounted on a tractor, the tractor is driven through the female rows, the N plants are touched and killed by the electrical charge in the metal rod leaving a pure stand of d plants.

4. A variety of devices can be engineered in which a detector mounted on the tractor triggers a second device which removes the plant which causes the triggering, in this case an N plant. Devices such as these can take many forms. Any such device is included in use for the invention.

5. Chemical treatment: This technique uses a chemical to restore fertility in the dwarf plants without genetically altering the line. dN seed is planted in an isolated increase field, the N plants removed manually, and the d plants treated with gibberellic acid. The amount of chemical will vary, but will typically be 10 ppm or more. At anthesis, the d plants will be self fertile, though genotypically 100% df1/df1. The seed thus produced is male sterile. Part of the seed is planted and treated again with gibberellic acid, which is a d line increase. The rest of the seed is planted in a hybrid field as a pure breeding female. In this manner only two types of seed are part of the production program, d lines and S lines. N lines are eliminated from the process of seed production.

V. SEED STOCKS MAINTENANCE USING df1 GENE

The guidelines presented above regarding plant spacing and precision, planting ratios, isolation parameters and use of bees apply to dN increases just as they do to hybrid increases. The different ways of increasing dN lines are as follows:

1. Plant the parental dN line in an isolated field, with no plants rogued prebloom. Off-type plants are rogued at or before anthesis. The N plants pollinate the d plants in the field. After pollination is finished the N plants are hoed out of the field, and moved away from the d plants to avoid accidental seed mixing. At maturity the d line is harvested mechanically.

2. Plant the dN line as described above in paragraph 1 until flowering is completed. At maturity separate the d plants manually and thresh them. This method works well in small increases and is also an option in larger increases.

3. Plant the dN line using the production techniques for a hybrid field. It will often be best to plant the seed to be used as N plants 5-7 days after the seed to be used as d plants. In the rows intended to be used as females, rogue the N plants prebloom leaving only d plants. After flowering, remove the N rows by chopping them out, and mechanically harvest the d line.

4. In the case of single cross increases, the two parental lines are planted following the techniques used in hybrid production. The pollinator variety will often need to be split planted with the female variety. The line used as the single cross d line is rogued identically to the d line in a hybrid field. The N line is not rogued at all. There will be d plants in the N line, but these will have no bearing on the production of the single cross female since they are sterile. At bloom, pollen from the N line crosses onto the sterile d plants to create the single cross dN line. After pollination the N line is cut from the field and the d line is harvested at maturity.

5. S lines are increased in a manner identical to those currently used for inbred commercial varieties which are well known to one of skill in the art.

VI. MAINTAINING PURITY OF HYBRIDS AND dN LINES

The purity of hybrid seed and dN seed should be carefully maintained. Seed samples from all production increases should also be grown out to monitor contamination from off type or nonhybrid plants. The three major sources of contamination are d plants that set selfed seed, N plants that escape roguing, and pollen originating outside the production field. In hybrid growouts the primary test of purity is to determine the percentage of non-hybrid dwarf plants in the growout sample. This is done by planting the hybrid seed samples in a growout, counting the number of dwarf plants, comparing this with the total number of plants and thus calculating the percentage of hybrid seed. In this way dwarf plants originating from selfed sterile plants and crosses of rogue N plants onto sterile plants can be monitored. Contamination from selfed N plants and outside pollen sources is difficult to see in a growout since the growth habit of safflower is such that vigor differences in individual plants are not easily distinguished. Only in cases in which the female has a genetic recessive gene while the S line or the foreign pollen source has the dominant gene can non-hybrid off types be identified in the growout. In dN growouts the characteristics to note are the d to N ratio, which cannot vary significantly from 1:1, and other general plant characteristics such as off-type plants or genetically incorrect plants. The latter techniques are well known in other hybrid crops.

In order to renew pure breeding dN lines, progeny testing is used. When a dN increase needs repurification, individual open pollinated (OP) dwarf sterile plants are selected. In the next generation, seed from each selection is grown individually and scored for segregation ratios and general plant type. Each selection should have 100 or more tested to have a statistically acceptable sample size. A chi-square test is made to determine acceptable from unacceptable selections. The remnant seed of unacceptable selections is discarded. Remnant seed of acceptable plant types is bulked for further increase.

VII. EXAMPLES OF LINES CARRYING df1 GENE

A. EXAMPLE 1:dN101 dN101 was derived from the original crosses made in the hybrid breeding program. The line is a linoleic type of safflower with an oil content of 36%. The fresh flower is yellow and the dried flower is orange. The plant spacing was 1 seed/foot between plants and 30 inches between rows. Stands were good. At anthesis, 50 d plants and 50 N plants were randomly selected. Notes were taken on the characteristics listed in Table 4.

The measurement's in Table 4 are subdivided into three sections: (1) those affected by the dwarf character of df1, (2) those affected by the sterile nature of df1, and (3) those unaffected by df1.

TABLE 4

| COMPARISON OF DWARF VS. NORMAL HEIGHT PLANTS IN LINE dN101 | | | | |
|---|---|---|---|---|
| TRAIT | DWARF (df1/df1) | NORMAL (DF1/df1) | DWARF/NORMAL (%) | t-test |
| DWARF CHARACTERISTICS | | | | |
| HEIGHT (in) | 11.6 | 21.2 | 55 | ** |
| BRANCH NO. | 12 | 14 | 86 | ** |
| INTERNODE LENGTH (in) (HGT/BR. NO.) | 0.9 | 1.5 | 60 | — |
| PLANT WEIGHT (g) | 118 | 167 | 71 | ** |
| TOTAL HEAD NO. | 46 | 55 | 84 | * |
| HEAD DIAMETER | 2.1 | 2.3 | 91 | ** |
| STERILITY CHARACTERISTICS | | | | |
| SEED WEIGHT; 100 SEEDS (g) | 5.03 | 4.19 | 120 | ** |
| SEED WEIGHT; 10 OP HEADS (g) | 7.1 | 16.5 | 43 | ** |
| SEED NO.; 10 SELF HEADS | 1.2 | 65.7 | 1.8 | ** |
| OIL CONTENT | 32.2 | 36.0 | 89 | ** |
| SEED LENGTH (mm) | 8.59 | 8.32 | 103 | ** |
| SEED WIDTH | 3.78 | 3.49 | 108 | ** |
| UNAFFECTED CHARACTERISTICS | | | | |
| SPINE LENGTH (mm) | 2.7 | 2.6 | 104 | NS |
| SPINE NO. | 14 | 13.9 | 100 | NS |
| SPINE INDEX (LENGTH × NO.) | 37.8 | 36.1 | 105 | — |

The dwarf plants in d101 were 55% the size of the normal plants. The height difference is accounted for largely by the shorter internode length in the dwarf plants (60% less) and the lower branch number (14% fewer). The lower head number in the dwarf plants is accounted for primarily by the lower branch number.

Head diameter was significantly lower in the dwarf plants.

The sterility of dwarf plants was plainly seen in the seed number of 10 selfed heads. Dwarf plants are 98% self sterile; open pollinated sterile plants also set fewer seed. The seed weight of 10 OP heads divided by 10 provides the average weight per head. This figure divided by the average weight per seed determines the number of seeds per head. From Table 4 this is determined to be 14 seeds per head for the open pollinated d line and 39 seeds per head for the N line. The seed that is set in the dwarf plants grew a thicker hull resulting in larger seed. This is reflected in the higher 100 seed weight and larger and thicker seed in the dwarf. Finally, the thicker seed coat caused a lower oil content in the dwarf plants. Kernel size remained about the same while the hull, which contains virtually no oil, grew larger, resulting in oil content about 4% lower in dwarf plants.

Spine length and spine width are slightly greater in dwarf plants, but not significantly greater. A greater spine index results, but the increase is not large. Seed dN101 is on deposit at the American Type Culture Collection (ATCC) located at 12301 Parklawn Drive, Rockville, Md. 20852, USA, under deposit accession number ATCC 75807.

B. EXAMPLE 2:dN102 dN102 was also derived from the original crosses made in the program. dN102 is an oleic line which has an oil content of 36%. Both the fresh and dried flower are yellow. dN102 was first increased in 1991. In 1992, a larger increase was grown. This increase was planted on May 1, 1992. The seed was planted at a wide spacing in order to maximize the total seed return. As with dN101, 50 d plants and 50 N plants were selected from the field. The spacing was very wide in this increase, more that two feet separated each plant. The numbers resulting from dN102 were essentially unaffected by neighboring plants. Data for dN102 are presented in Table 5.

primarily to lower head number (73%) and lower seed set (as observed in the seed weight (60%) of 10 open pollinated heads). Head diameter was again significantly lower in the dwarf plants.

The differences due to sterility in dN102 were also significant. Seed weight of 10 open pollinated heads as mentioned above was lower in the dwarf due to a lower crossing percentage in sterile d plants than selfing and crossing in fertile N plants. The d line averaged 18.6 seeds/head and the N line 41.5 seeds/head. 100 seed weight, seed length, and seed width were higher in dwarf plants while oil content is lower.

Spine length was again nonsignificant in dN102, but spine number was significantly higher in the dwarf plants. Seed dN102 is on deposit at the American Type Culture Collection (ATCC) located at 12301 Parklawn Drive, Rockville, Md. 20852, USA, under deposit accession number ATCC 75808.

C. COMPARATIVE DATA OF dN101 AND dN102

The actual values between dN101 and dN102 were quite different. This is of course expected since the two lines are genotypically distinct. Of interest is the effect of the df1 gene in relative differences between d and N plants of the two lines. These effects are quite similar between dN101 and dN102. The effect of df1 on plant height, branch number, internode length, and head diameter is almost identical in d plants compared to N plants in dN101 and dN102 when the value of d plants is expressed as a percent of N plants. The percentage difference for plant weight is 10% and the total head number is 11%. These larger deviations are due to greater environmental variability in these traits. The coefficient of variability for plant weight is 39% and for head diameter it is 36%. Other dwarfness traits have CV's ranging from 12% for plant height to 23% for branch number.

The comparative statistics between dN101 and dN102 regarding sterility characteristics were also similar. 100 seed weight, oil content, seed length and seed width are all within a few percentage points. Only the

TABLE 5

| COMPARISON OF DWARF VS. NORMAL HEIGHT PLANTS IN LINE dN102 | | | | |
|---|---|---|---|---|
| TRAIT | DWARF (dfl/dfl) | NORMAL (Dfl/dfl) | DWARF/NORMAL (%) | t-test |
| DWARF CHARACTERISTICS | | | | |
| HEIGHT (in) | 8.7 | 16.4 | 53 | ** |
| BRANCH NO. | 10.4 | 12.3 | 85 | ** |
| INTERNODE LENGTH (in) (HGT/BR. NO.) | 0.89 | 1.61 | 55 | — |
| PLANT WEIGHT (g) | 158 | 260 | 61 | ** |
| TOTAL SEED WEIGHT (g) | 31.2 | 85.8 | 36 | ** |
| TOTAL HEAD NO. | 88 | 121 | 73 | ** |
| HEAD DIAMETER | 2.1 | 2.4 | 88 | ** |
| STERILITY CHARACTERISTICS | | | | |
| SEED WEIGHT; 100 SEEDS (g) | 5.16 | 4.19 | 123 | ** |
| SEED WEIGHT; 10 OP HEADS (g) | 10.4 | 17.4 | 60 | ** |
| OIL CONTENT | 31.7 | 36.4 | 87 | ** |
| SEED WIDTH (mm) | 3.93 | 3.60 | 109 | ** |
| UNAFFECTED CHARACTERISTICS | | | | |
| SPINE LENGTH (mm) | 2.5 | 2.4 | 104 | NS |
| SPINE NO. | 13.5 | 11.8 | 114 | ** |
| SPINE INDEX (LENGTH × NO.) | 33.7 | 28.3 | 119 | — |

Differences between d and N plants were again striking. Smaller internode length and fewer branches accounted for most of the height difference. The lower branch number accounted for most of the lower head number. Seed weight per plant was much lower in the d plants than in N plants. The lower seed yield was due seed weight of 10 open pollinated heads varied by a large amount. The coefficient of variability for the seed weight of 10 open pollinated heads is 33%, while for the other sterility traits it ranges from 5% to 12%. Environmental variability and varietal differences for crossing ability account for most of the variability.

Seed set in dN101 was 36% and in dN102 it was 45%, a 9% increase. This increase had little affect on other sterility characteristics. It is likely that until crossing percentages are much higher will the sterility effects begin to lessen, and not until they are near 100% will they disappear.

Spine length and number varied marginally between d plants and N plants in dN101 and dN102. Spine number in dN102 varied significantly. The trend in both cases was for larger and more spines in the d plants. Given the small size of the spines and the large numbers that would be necessary to make a determination it would be difficult to ascertain the effect of df1 on spine number and length.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A safflower seed that produces a dwarf, male sterile safflower plant that exhibits male sterility in combination with morphologically identifiable dwarfism which segregate pleiotropically as a single gene having the genotype designation df1/df1 and having ATCC Accession No. 75807 or ATCC Accession No. 75808.

2. A dwarf male sterile, safflower plate grown from the seed of claim 1.

3. A safflower plant having all the physiological and morphological characteristics of the plant of claim 2.

4. A hybrid safflower seed produced from a cross in which the female parent is the safflower plant of claim 2 or claim 3.

5. A hybrid safflower plant that is a normal height, male fertile safflower grown from the seed of claim 4.

6. A method of producing a hybrid safflower seed comprising the steps of:
    (a) planting a dwarf, male sterile safflower plant ("d") as the female parent in the hybrid safflower seed production, wherein said "d" plant has the genotype df1/df1 and has ATCC Accession No. 75807 or ATCC Accession No. 75808; and,
    (b) planting a safflower plant ("S") that is male fertile as the male parent in the hybrid safflower seed production; and
    (c) crossing said "d" plant with said "S" plant and collecting hybrid seed from the "d" plants for use as hybrid seed.

7. A method of maintaining dwarf, male sterile safflower seeds for use in producing hybrid safflower seed comprising the steps of:
    (a) planting a dwarf, male sterile safflower plant ("d") as the female parent in the safflower seed production, wherein said "d" plant has the genotype df1/df1 and has ATCC Accession No. 75807 or ATCC Accession No. 75808; and
    (b) planting a safflower plant ("N") that is heterozygous for the gene df1, wherein said "N" plant is male fertile and is the male parent in the safflower seed production;
    (c) crossing said "d" plant with said "N" plant such that approximately one half of the resulting seed ("dN") from the female safflower plant is homozygous for the gene df1 and the other half of said seed is heterozygous for the gene df1;
    (d) planting said "dN" safflower seed and growing said thus produced plants wherein one-half of said safflower plants will be dwarf, male sterile plants ("d") having the gene df1 and the other half of said safflower plants will be male fertile and heterozygous ("N") for said gene df1;
    (e) allowing pollen from the male fertile "N" plants to pollinate the male sterile "d" plants;
    (f) selecting for plants that are homozygous for the gene designated df1 as determined by its dwarf phenotype which will have produced seed that is heterozygous ("dN") for the gene df1; and,
    (g) collecting dN seed from the selected dwarf plants for use as the female parent of a hybrid safflower seed.

8. The method of claim 7 further comprising harvesting the "N" seed produced from step (e) resulting from any self pollination of the male fertile "N" plants, wherein said "N" seed may be used in hybrid seed production.

9. A method of producing hybrid seed comprising the steps of:
    (a) planting "dN" safflower seed of claim 9 as the female parent in the hybrid safflower seed production, wherein said planted "dN" seed produces plants wherein one-half of said safflower plants will be dwarf, male sterile plants ("d") having the gene df1 and the other half of said safflower plants will be male fertile, normal sized plants and heterozygous ("N") for said gene df1;
    (b) planting a safflower variety ("S") as the male parent in the hybrid safflower seed production;
    (c) removing "N" plants before anthesis leaving "d" plants and "S" plants;
    (d) producing a hybrid safflower seed from the cross of the dwarf male sterile female parent "d" and the safflower variety "S" as the male parent;
    (e) collecting seed from the "d" plants for use as hybrid seed.

10. A method of producing hybrid seed comprising the steps of:
    (a) planting "N" seed of claim 8 as the female parent of the hybrid safflower seed, wherein said "N" seed is heterozygous for the gene df1 and thus will produce plants that are dwarf, male sterile ("d") and plants that are male fertile, and normal height;
    (b) removing normal height plants from the female seed planting and growing said "d" plants;
    (c) crossing said "d" plants with a safflower variety "S" plant as the male parent in the hybrid safflower seed production; and
    (c) crossing said "d" plant with said "S" plant and collecting hybrid seed from the "d" plants for use as hybrid seed.

11. A method of creating new dwarf male sterile "dN" parental lines comprising the steps
    (a) crossing a first and second safflower plant, as parent plants, wherein said first safflower plant is a dwarf male sterile plant ("d"), having the gene df1 and having the ATCC Accession No. 75807 or ATCC Accession No. 75808 and said second safflower plant is a safflower variety ("S");
    (b) selecting plants from segregating generations derived from step (a) that exhibit the dwarf phenotype;
    (c) crossing said selected dwarf plants from step (b) and continuing to select and cross plants exhibiting the dwarf male sterile phenotype to produce a parental line ("dN") that is heterozygous for said gene df1.

12. The method of claim 11, step (a) wherein one parent safflower plant is homozygous for the gene df1 and the other parent safflower plant is heterozygous for the gene df1.

13. The method of claim 11, step (a) wherein both safflower parent plants are heterozygous for the df1 gene.

14. A safflower seed having the genotype designation df1/df1 and having ATCC Accession No. wherein a safflower plant grown from said seed contains a gene which exhibits male sterility in combination with morphologically identifiable dwarfism, 75807 or ATCC Accession No. 75808 wherein the dominant form of the gene, DF1, produces a plant that is male fertile and of normal height; and the recessive form of the gene, df1, produces a plant that is both male sterile and of dwarf stature, wherein male sterility and dwarfness segregate in said gene.

* * * * *